United States Patent [19]

Takano

[11] Patent Number: 5,258,601

[45] Date of Patent: Nov. 2, 1993

[54] CAPILLARY RHEOMETER WITH TEMPERATURE CONTROLLER FOR MAINTAINING UNIFORM TEMPERATURE DISTRIBUTION OF SAMPLE

[75] Inventor: Susumu Takano, Shiga, Japan

[73] Assignee: Shimadzu Corporation, Kyoto, Japan

[21] Appl. No.: 778,658

[22] Filed: Oct. 18, 1991

[30] Foreign Application Priority Data

Oct. 30, 1990 [JP] Japan .................................. 2-293468

[51] Int. Cl.$^5$ ............................................. H05B 1/02
[52] U.S. Cl. .................... 219/486; 219/485; 219/494; 219/508; 307/40; 374/110
[58] Field of Search ............. 219/494, 497, 483–486, 219/506, 501, 499, 508; 307/38–41; 374/30, 32, 110

[56] References Cited

U.S. PATENT DOCUMENTS

| | | | |
|---|---|---|---|
| 4,587,837 | 5/1986 | Newbould . | |
| 4,599,507 | 7/1986 | Hishikari et al. | 219/481 |
| 4,657,572 | 4/1987 | Desai et al. | 219/481 |
| 4,680,958 | 7/1987 | Ruelle et al. . | |
| 5,053,604 | 10/1991 | Escaravage et al. | 219/483 |

FOREIGN PATENT DOCUMENTS

0089130 9/1983 European Pat. Off. .

Primary Examiner—Mark H. Paschall
Attorney, Agent, or Firm—Wegner, Cantor, Mueller & Player

[57] ABSTRACT

In a capillary rheometer including: a furnace comprising a plurality of furnace zones and having a sample bore with a capillary connected to the lower end thereof; a plurality of heaters for heating the furnace zones thereby to heat a sample in the sample bore; and a plunger for extruding the heated sample through the capillary; a plurality of temperature sensors are provided for detecting the temperatures of the furnace zones, and the temperature characteristics of the furnace zones related to the temperature of the inner wall of the sample bore are obtained and stored in a controller. With a set objective temperature level to which the sample in the sample bore is to be heated, the controller determines on the basis of the stored temperature characteristics data the temperature of each of the furnace zones corresponding to the set objective temperature level, and controls the heaters so that the temperature detected by each of the temperature sensors coincides with the determined temperature of the corresponding one of the furnace zones. A temperature measuring rod is also provided, which is adapted for insertion into the sample bore to accurately measure the temperature of the inner wall of the sample bore.

15 Claims, 5 Drawing Sheets

CAPILLARY RHEOMETER WITH TEMPERATURE CONTROLLER FOR MAINTAINING UNIFORM TEMPERATURE DISTRIBUTION OF SAMPLE

BACKGROUND OF THE INVENTION

This invention relates to an extrusion type capillary rheometer for measuring the rheological properties, such as, flow property, viscosity and molecular weight distribution of materials such as plastics, ceramics and rubber. The invention also relates to a temperature measuring device for measuring the temperature of the sample bore of the rheometer.

Japanese Unexamined Utility Model Publication No. 59-101196 (Appln. No. 57-202566) discloses a rheometer of this type which comprises an electric furnace provided with a bore for a sample to be inserted into and a capillary connected to the lower end of the sample bore. The body of the furnace is sectioned into a plurality of zones, which are provided with individual heaters to heat the sample in the sample bore, and individual temperature sensors for detecting the temperatures of the respective furnace zones. One of the furnace zones is selected as a reference zone, and a controller controls the heater of the reference zone by a control signal so as to keep the zone at a predetermined temperature, and applies the control signal to the temperature controllers for the other furnace zones thereby to keep the temperature distribution of the whole furnace uniform. Then a plunger is inserted into the sample bore to extrude the heated sample out of the furnace through the capillary thereby to measure the rheological properties of the sample by the speed of movement of the plunger.

Japanese Unexamined Utility Model Publication No. 3-40550 (Appln. No. 1-101648) discloses a rheometer in which a separate barrel formed with a sample bore is disposed in the central portion of an electric furnace provided with heaters so as to make assemblage and maintenance of the furnace easy.

There are problems, however, to be solved in the known arrangements. Since there is a difference in temperature between the furnace zones and the inside of the sample bore, in the arrangement that the temperatures of the zones are merely controlled so as to coincide with the reference temperature, it is impossible to make the temperature distribution of the sample itself uniform because of thermal interference between the different furnace zones. In the arrangement that a separate barrel is disposed in the furnace, if the barrel is of a single body, a similar thermal interference occurs to prevent the temperature distribution in the sample from becoming uniform.

SUMMARY OF THE INVENTION

Accordingly, the primary object of the invention is to provide a capillary rheometer provided with a temperature controller capable of keeping the sample itself at a desired temperature while making the temperature distribution of the sample substantially uniform.

Another object of the invention is to provide a temperature measuring device capable of accurately measuring the temperature of the inner wall of the sample bore in the rheometer.

The invention provides a capillary rheometer which comprises:

a) a furnace comprising a plurality of furnace zones so arranged as to suppress mutual thermal interference and provided with a central sample bore into which a sample to be tested is inserted, with a capillary connected to the lower end of said central sample bore;

b) a plurality of heaters each provided for one of said furnace zones to heat said sample in said sample bore;

c) plunger means for imposing a predetermined load on said heated sample to extrude the same through said capillary;

d) a plurality of temperature sensors each provided in one of said furnace zones for detecting the temperature thereof;

e) means for storing the temperature characteristics of said furnace zones related to the temperature of the inner wall of said sample bore;

f) means for setting an objective value of the temperature of said inner wall of said sample bore; and g) heater controlling means for determining on the basis of said temperature characteristics data stored in said storing means the temperature of each of said furnace zones corresponding to said set objective temperature value, and controlling energization of said heaters so that the temperature detected by each of said temperature sensors coincides with said determined temperature of the corresponding one of said furnace zones.

When the setting means is operated to set an objective value of the temperature of the inner wall of the sample bore, the heater controlling means determines the temperatures of the furnace zones corresponding to the objective temperature on the basis of the temperature characteristics data stored in the storing means, and controls the heaters so that the temperatures detected by the temperature sensors in the furnace zones coincide with the determined temperatures thereby to maintain the temperature of the inner wall of the sample bore and cosequently that of the sample uniformly at the set objective temperature.

In accordance with the invention, inside the furnace there is provided a hollow cylindrical barrel, in which a tubular inner liner is fitted. The inner liner is divided into a plurality of sections along the length thereof thereby to suppress mutual thermal interference on the inner surface of the barrel between the furnace zones and to improve the uniformity of temperature distribution in the sample.

The invention also provides a temperature measuring device for use in the rheometer to measure the temperature of the sample bore of the rheometer. The device comprises a cylindrical stem adapted for insertion into the sample bore defined by the inner liner of the barrel of the rheometer so as to be able to be pulled out therefrom, and a plurality of temperature sensors provided on the outer surface of the stem at those positions thereof which correspond to the furnace zones when the device is inserted into the sample bore of the rheometer. When the device is inserted into the sample bore, the temperature sensors on the outer surface of the stem contact the inner wall surface of the sample bore at the positions corresponding to the furnace zones to measure the temperatures thereof accurately.

PREFERRED EMBODIMENT OF THE INVENTION

Figure 2:
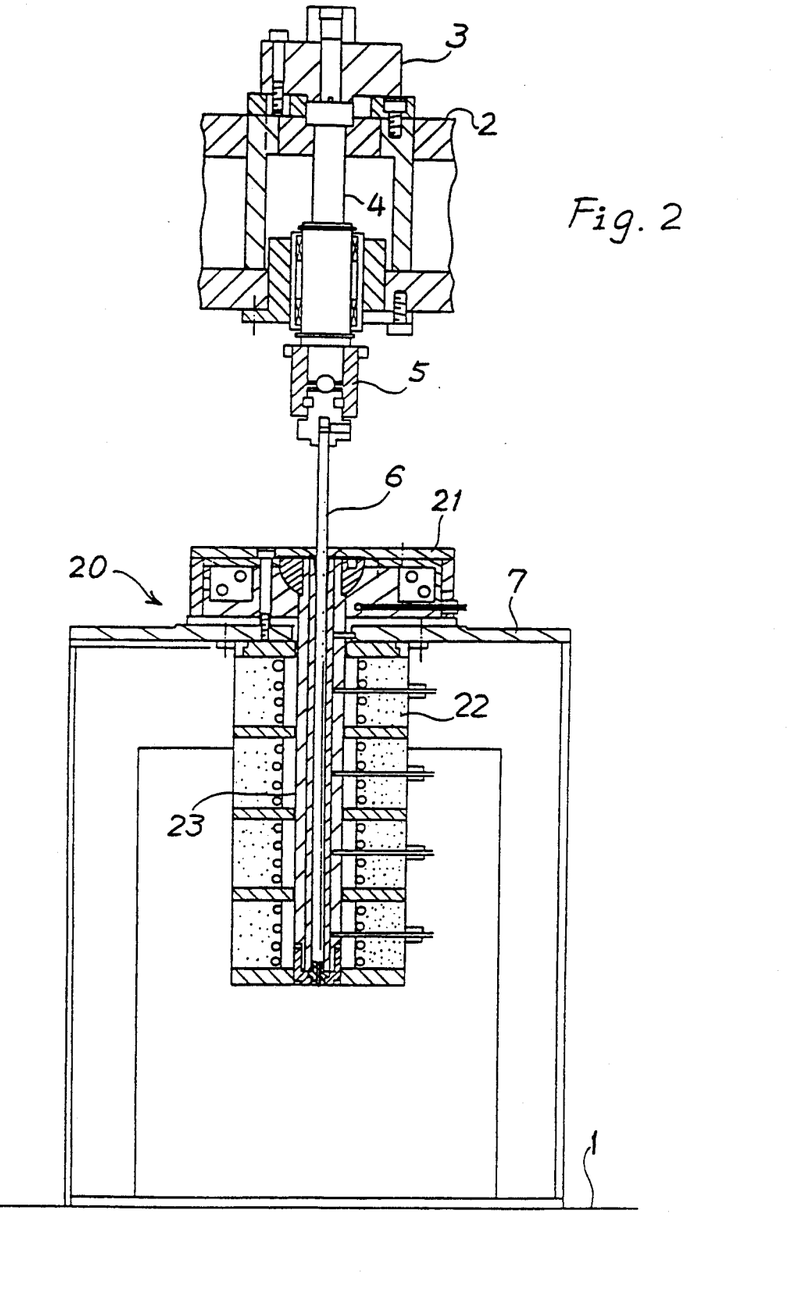
FIG. 2 is a front view, partially in vertical section, of the rheometer mounted on a material testing machine.

Referring to the drawings, first to FIG. 2, there is shown a part of a material testing machine including a table 1, a crosshead 2 carried by a spaced pair of columns, not shown, so as to be vertically movable, and a load cell 3 provided on the crosshead for detecting the load imposed on a sample to be tested. A load rod 4 is connected to the load cell 3, extends vertically downward through the crosshead 2, and carries at its lower end a connector 5 to which a plunger 6 for extruding a sample is connected.

The table 1 supports a gate-shaped support 7, from which an electric furnace 20 hangs. As shown in detail in FIG. 3, the furnace 20 comprises an upper furnace portion 21 fixed on the upper side of the support 7, a lower main furnace portion 22 fixed on the under side of the support 7, and a central barrel 23 extending concentrically through the upper and lower furnace portions 21 and 22 so as to connect the two portions into a single furnace.

Figure 3:
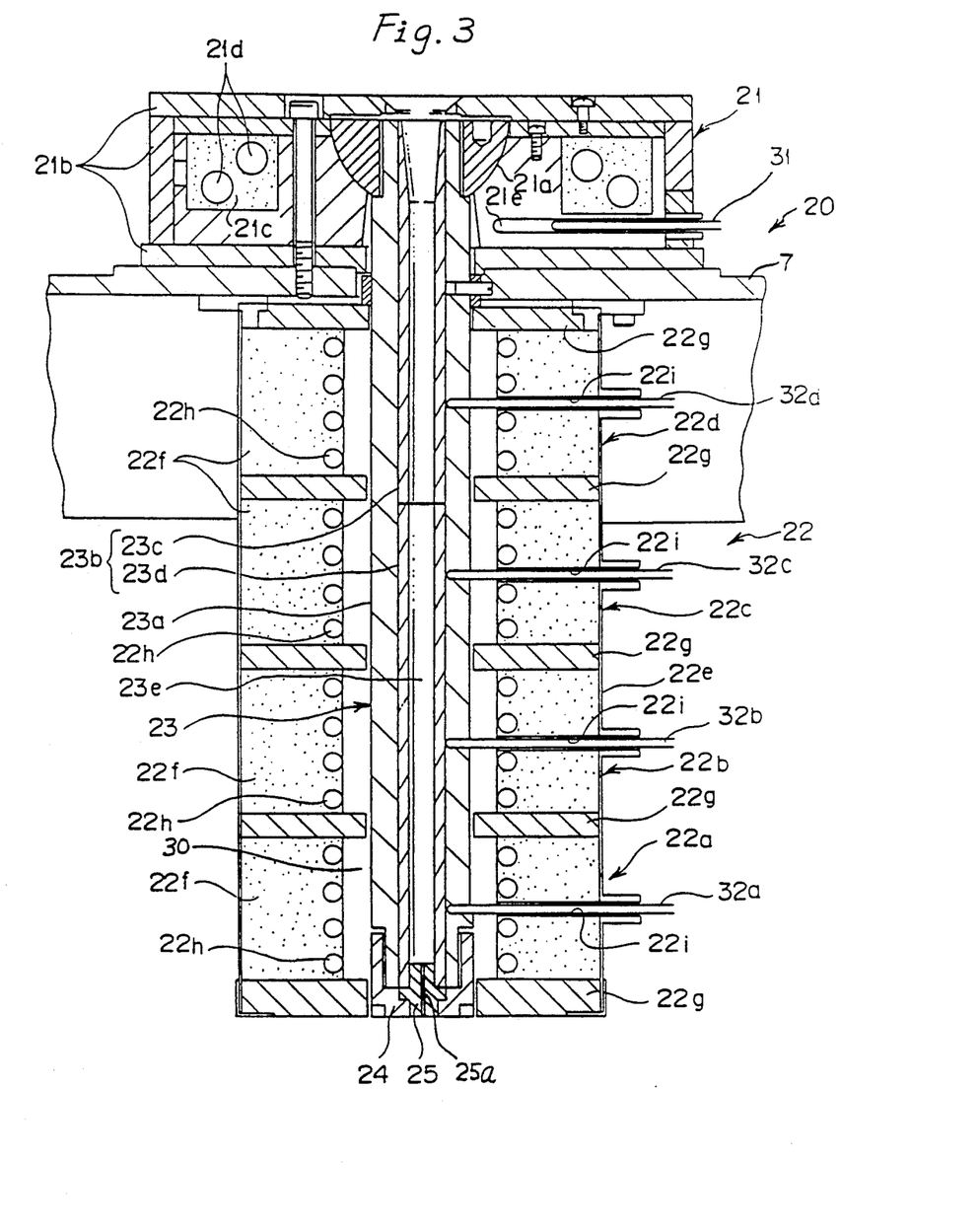
FIG. 3 is a sectional view of the furnace included in the rheometer of the invention.

The barrel 23 comprises an outer tubular member 23a and an inner liner 23b closely fitted into the outer tubular member 23a. The upper furnace portion 21 is provided at its central portion with a semi-spherical bearing 21a, into which the upper end of the outer tubular member 23a is screwed, so that the barrel hangs from the bearing 21a to extend through the furnace.

The inner liner 23b defines an axial bore 23e into which a sample to be tested is to be inserted. A plug 25 formed with a capillary 25a is fitted into the lower end of the sample bore 23e and secured by a nut 24 screwed to the lower end of the barrel 23 so that the sample bore 23e communicates with the capillary 25.

In the illustrated embodiment, the inner liner 23b is made up of an upper liner section 23c and a lower liner section 23d, which are separately formed and shrinkfitted into the outer tubular member 23a of the barrel 23 so as to form a continuous liner. The arrangement that the two separate liner sections are combined in the outer tubular member 23a not only makes it easy to form the sample bore 23e and improve the accuracy of its inner diameter but also enables suppression of thermal interference between the upper and lower furnace zones 22d and 22c on the opposite sides of the border between the upper and the lower liner sections 23c and 23d, as will be described in detail hereinafter.

The upper furnace portion 21 has an upper, a lower and a circumferential wall 21b of thermal insulator, which define an inner annular space filled with cement 21c, with a pair of concentric Nichrome ring heaters 21d embedded in the cement 21c. The upper furnace portion 21 is formed with a radial hole 21e, into which a temperature sensor 31 is inserted. The sensor 31 is provided at its forward end with a thermocouple or thermistor.

The lower furnace portion 22 comprises a hollow cylindrical casing 22e and four annular members 22f of cement piled up one upon another in the casing 22e. Each of the annular members 22f is formed with a central through hole of an inner diameter greater than the outer diameter of the previously described barrel 23. The holes of the annular members 22f are axially aligned to form a central bore, in which the barrel 23 is disposed, with an air space 30 formed between the inner circumferential surface of the central bore and the outer circumferential surface of the barrel 23. A plurality of annular members 22g of thermal insulator are provided, one in each of the top and bottom portions of the hollow cylindrical casing 22e as well as between each adjacent two of the annular members 22f of cement. The annular members 22g of thermal insulator have their inner circumferential edges projecting radially inwardly into the air space 30 as far as adjacent the outer circumferential surface of the barrel 23.

In each of the annular cement members 22f and adjacent the inner circumferential surfaces thereof there are embedded four Nichrome ring heaters 22h vertically equidistantly spaced part from each other. The sample in the bore 23e is heated by the ring heaters 22h through the barrel 23.

Those sections of the lower furnace portion 22 which correspond to the four annular cement members 22f will be referred to as the furnace zones 22a, 22b, 22c and 22d from the bottom upward. Each of the furnace zones 22a to 22d is provided with a radial bore 22i, into which a temperature sensor 32a to 32d is inserted as far as the forward end thereof passes through a corresponding radial bore formed in the barrel 23a to contact the outer circumferential surface of the inner liner 23b for detection of the temperature of the liner 23b. The temperature sensors 32a to 32d are provided at their respective front ends with a thermocouple or thermistor.

Figure 4A:
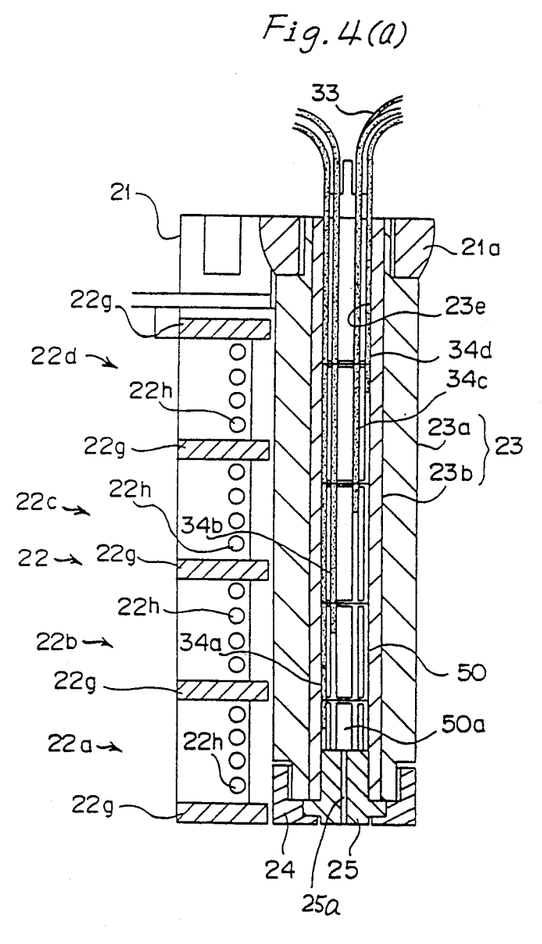
FIG. 4(a) is a sectional view of a part of the furnace with a temperature measuring rod of the invention inserted into the sample bore of the rheometer.
Figure 4B:
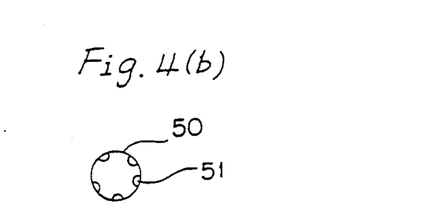
FIG. 4(b) is an axial end view of the temperature measuring rod.
Figure 4C:
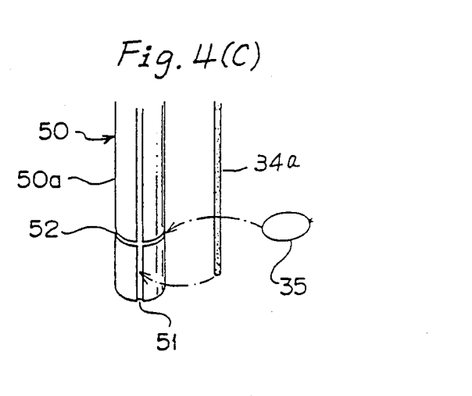
FIG. 4(c) is a perspective view of part of the temperature measuring rod.

FIG. 4 shows a temperature measuring rod 50 adapted for insertion into the sample bore 23e of the barrel 23. The rod 50 comprises a stem 50a formed on the outer circumferential surface thereof with a plurality, say, five axially extending parallel grooves 51 arranged at equiangular positions about the circumference of the stem, and a plurality, say, four circumferential grooves 52 spaced a suitable distance apart from each other axially of the stem. Temperature sensors 33, 34a, 34b, 34c and 34d are fitted in the axial grooves 51, respectively, and secured therein by a tungsten wire 35 wound in each of the circumferential grooves 52.

The temperature sensors 33 and 34a to 34d have such lengths that when the temperature measuring rod 50 is inserted into the sample bore 23e of the barrel 23, the respective forward ends of the temperature sensors 33 and 34a to 34d contact those portions of the wall surface of the sample bore 23e which correspond to the upper furnace portion 21 and the furnace zones 22a to 22d of the lower furnace portion 22, respectively, so as to measure the temperatures of those surface portions of the sample bore.

Figure 1:
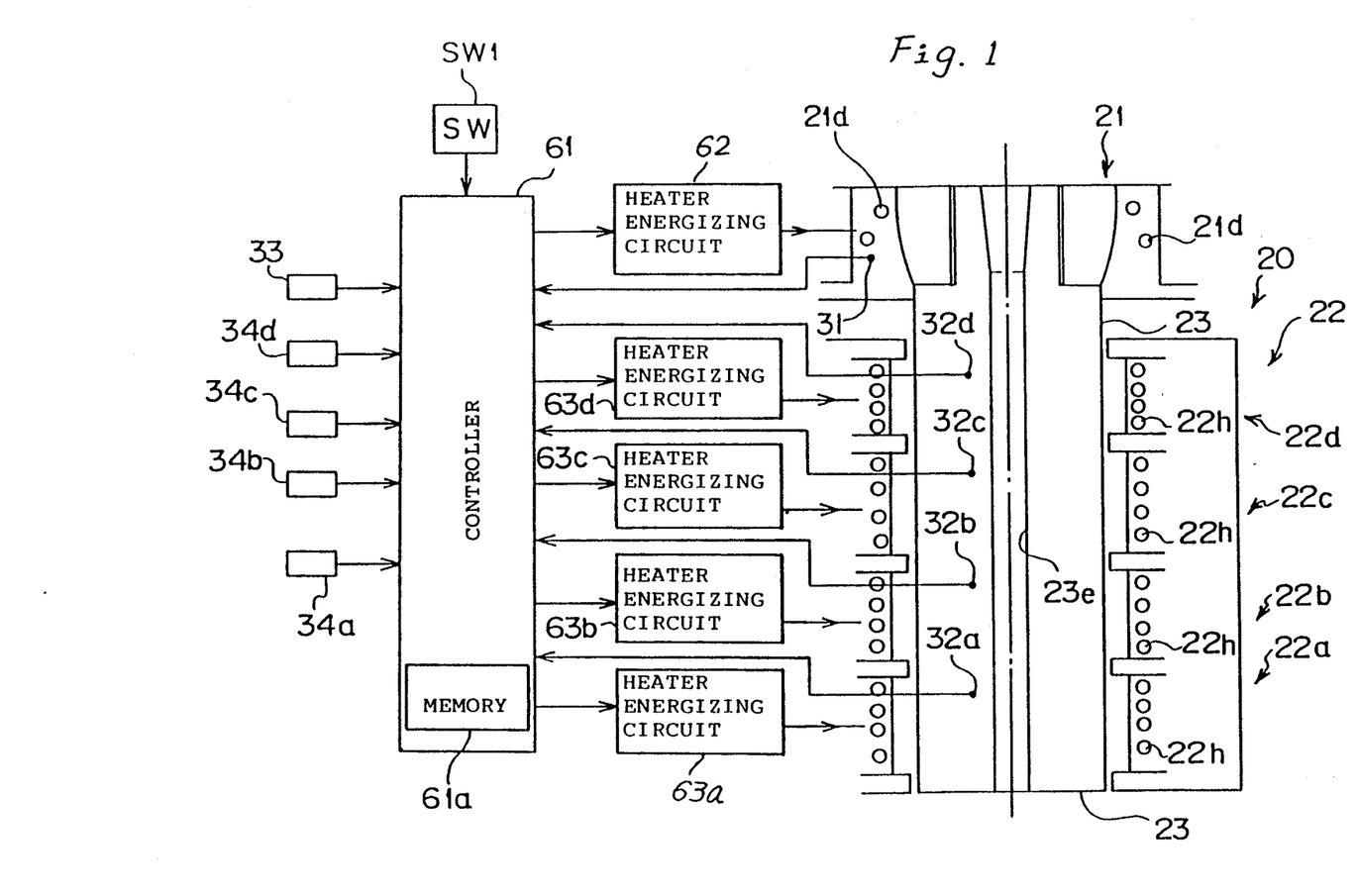
FIG. 1 is a block diagram of a control system of a rheometer constructed in accordance with the invention.

FIG. 1 shows a system for controlling the temperature of the furnace. The system comprises a controller 61 which includes a memory 61a and a central processing unit not shown. The temperature sensors 31 and 32a to 32d are connected to the controller 61 so that the output signals from the sensors 31 and 32a to 32d corresponding to the detected temperatures are applied to the controller 61. Also connected to the controller 61 are circuits 62 and 63a to 63d for energizing the ring heaters 21a and 21h for the upper furnace portion 21 and the four furnace zones 22a to 22d of the lower furnace portion 22, respectively.

A switch $SW_1$ for setting an objective temperature to which a sample to be tested is to be heated is also connected to the controller 61, to which the temperature sensors 33 and 34a to 34d of the measuring rod 50 are connectable. The memory 61a stores the temperature characteristics of those portions of the barrel 23 which correspond to the upper furnace portion 21 and the furnace zones 22a to 22d, related to the temperature of the inner wall of the sample bore 23e. The temperature characteristics are obtained in a manner to be described below in detail. When a sample is to be tested, the controller 61 controls the energizing circuits 62 and 63a to 63d in accordance with the stored temperature characteristics data thereby to control the temperature of the sample at a required level.

As previously mentioned, the temperature measuring rod 50 provided with the temperature sensors 33 and 34a to 34d is inserted into the sample bore 23e of the barrel 23, so that the temperature sensor 33 contacts the inner wall surface of that portion of the bore 23e which corresponds to the upper furnace portion 21 while the temperature sensors 34a to 34d contact the inner wall surface of those portions of the bore 23e which correspond to the furnace zones 22a to 22d, respectively, of the lower furnace portion 22.

Then the heater energizing ciruicts 62 and 63a to 63d are actuated to energize the ring heaters 21a and 22h until the outputs from all of the temperature sensors 33 and 34a to 34d indicate, say, 100° C., whereupon the temperatures detected by the temperature sensor 31 in the upper furnace portion 21 and the temperature sensors 32a to 32d in the furnace zones 22c to 22d of the lower furnace portion 22, that is, the temperatures in the five different portions of the inner liner 23b of the barrel 23 for the set temperature of 100° C., are read and stored in the memory 61a.

In a similar manner, the energizing circuits 62 and 63a to 63d are so controlled that the temperatures detected by all of the sensors 33 and 34a to 34d of the temperature measuring rod 50 become, say, 150° C., and the temperatures then detected by the sensors 31 and 32a to 32d for the set temperature of 150° C. are recorded. The above operation is repeated with the energizing circuits 62 and 63a to 63d being so controlled that the temperatures detected by all of the sensors 33 and 34a to 34d of the temperature measuring rod 50 become 200° C., 250° C., . . . , respectively, and the temperatures detected by the sensors 31 and 32a to 32d for each of the set temperatures of 200° C., 250° C., . . . being stored in the memory 61a.

Figure 5:
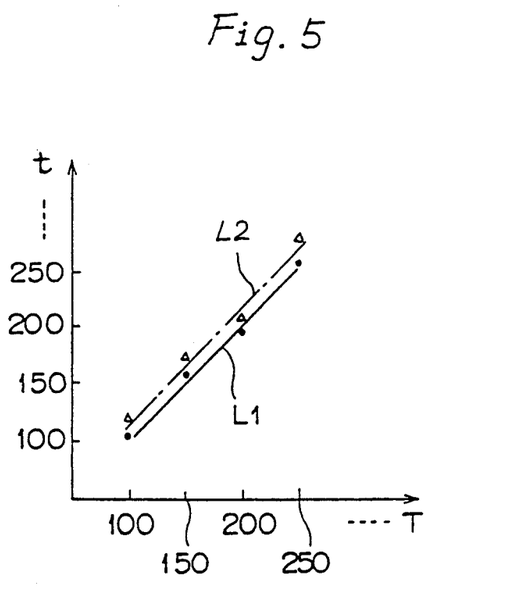
FIG. 5 is a graph showing some of the temperature characteristic lines of the furnace zones stored in the control system of FIG. 1.

From the data obtained in the above manner charcteristic lines are plotted as shown in FIG. 5, wherein the set temperature T detected by the sensors 33 and 34a to 34d of the temperature measuring rod 50 is taken along the abscissa, and the temperature t detected by each of the sensors 31 and 32a to 32d is taken along the ordinate. In particular, the temperatures t detected by one of the sensors 31 and 32a to 32d, say, the sensor 31 are plotted for the set temperatures T of 100° C., 150° C., 200° C., 250° C., . . . to obtain a characteristic line $L_1$.

In a similar manner, the temperatures t detected by each of the other sensors 32a to 32d are plotted for the set temperatures T of 100° C., 200° C., 250° C., . . . to obtain similar characteristic lines $L_2$, $L_3$, $L_4$ and $L_5$, only one of which is shown at $L_2$ in FIG. 5 for simplicity of illustration. These characteristic lines are stored in the memory 61a of the controller 61.

In operation, a sample to be tested is put in the sample bore 23e of the barrel 23, and the switch $SW_1$ is operated to set an objective temperature T to which the sample is to be heated. The controller 61 determines the temperatures t corresponding to the set objective temperature T for the five furnace zones on the basis of the above-mentioned five characteristic lines stored in the memory 61a, and then controls the ring heaters 21d and 22h through the energizing circuits 62 and 63a to 63c, respectively, so that the temperatures detected by the temperature sensors 31 and 32a to 32d coincide with the determined temperatures t for the five furnace zones, respectively. In this manner, it is possible to cause the temperature of the inner wall surface of the sample bore 23e of the barrel 23 and consequently that of the sample itself in the bore 23e to uniformly coincide with the objective temperature T. Then the crosshead 2 is driven to push the plunger 6 into the sample bore 23e to impose a predetermined load on the sample, which is extruded outside through the capillary 25a. The viscosity of the sample is calculated from the speed of the plunger driven in the above-mentioned manner for measurement of the fluidity of the sample.

In addition to the above-mentioned advantage that the temperature of the sample can be maintained uniformly at the set level, the invention has the following advantages.

First, since the inner liner 23b of the barrel 23 is divided into the upper and lower sections 23c and 23d, thermal interference in the inner surface of the barrel between at least the furnace zones 22c and 22d can be suppressed thereby to improve the uniformity of the temperature distribution of the sample.

Secondly, since the insulation ring 22g is interposed between each adjacent two of the annular members 22f of cement constitutting the furnace zones 22a to 22d can be suppressed thereby to improve the uniformity of the temperature distribution of the sample. Since the Nichrome ring heaters are used, the maximum temperature that is controllable can be higher than with the band heaters used in the invention disclosed in Japanese Unexamined Utility Model Publication No. 59-101196.

In the above embodiments, the memory 61a constitutes storing means; the switch $SW_1$, temperature setting means; and the controller 62 and the energizing circuits 63a to 63c, heater controlling means.

In the above embodiments, the inner liner 23b of the barrel 23 is divided into two sections. It may be divided into three or more sections. For example, the inner liner may be divided into five sections corresponding to the upper furnace portion 21 and the four furnace zones 22a to 22d of the lower furnace portion 22. This will suppress thermal interference in the inner surface of the barrel 23 between the furnace zones thereby to improve the uniformity of the temperature distribution in the sample being tested.

The number of the furnace zones is not limited to four as in the illustrated embodiment. The arrangement of the control system is not limited to that shown in FIG. 1, either.

In the apparatus of the invention, the memory 61a stores the temperature characteristics of the furnace zones related to the temperature of the inner wall of the sample bore in the furnace, and on the basis of the stored temperature characteristics data a control temperature to which each of the furnace zones is to be heated so as to attain the objective temperature in the sample bore is determined, whereupon the ring heaters are so controlled that the temperatures of the furnace zones coincide with the determined control temperature. This makes it possible to keep the temperature of the inner wall of the sample bore and consequently that of the sample therein uniform and at a required level.

Since the barrel 23 comprises a hollow cylindrical body and an inner liner fitted therein, which is divided into a plurality of sections in the axial direction thereof, it is possible to prevent thermal interference in the inner wall of the barrel between the furnace zones thereby to improve the uniformity of temperature distribution of the sample.

Since the temperature measuring rod to be inserted into the sample bore is provided on its circumferential surface with a plurality of sensors at different positions along the length of the rod, the temperature of the inner wall surface of the sample bore at different portions thereof corresponding to the furnace zones can be detected by merely inserting the rod into the sample bore only once and without troublesome operations.

In the illustrated embodiment, although the sensors 32a to 32d are so arranged that the sensing elements contact the outer circumferential surface of the inner liner 23b of the barrel 23, they need not necessarily contact the liner liner.

What I claim is:

1. A capillary rheometer comprising:
   (a) a furnace comprising a plurality of furnace zones so arranged as to suppress mutual thermal interference and provided with a central sample bore into which a sample to be tested is inserted, and a capillary connected to the lower end of said central sample bore;
   (b) a plurality of heaters each provided for one of said furnace zones to heat said sample in said sample bore;
   (c) plunger means for imposing a predetermined load on said heated sample to extrude the same through said capillary;
   (d) a plurality of temperature sensors each provided in one of said furnace zones for measuring the temperatures thereof;
   (e) means for storing the temperature characteristics of said furnace zones related to the temperature of the inner wall of said sample bore;
   (f) means for setting a reference value of the temperature of said inner wall of said sample bore;
   (g) heater controlling means for determining on the basis of said temperature characteristics stored in said storing means the temperature of each said furnace zones corresponding to said set reference temperature value, and controlling energization of said heaters so that the temperature detected by each of said temperature sensors coincides with said determined temperature of the corresponding one of said furnace zones, whereby the sample is uniformly heated.

2. The rheometer of claim 1, wherein said furnace comprises an upper furnace portion and a lower furnace portion composed of a plurality of furnace zones, said upper and lower furnace portions being mounted on the upper and under sides, respectively, of a crosshead of a material testing machine and having a central, axial bore which encloses a barrel provided with an inner liner defining said sample bore; and wherein said temperature sensors are disposed in said upper furnace portion and said furnace zones of said lower furnace portion.

3. The rheometer of claim 1, wherein said furnace comprises an upper furnace portion and a lower furnace portion composed of a plurality of furnace zones, said upper and lower furnace portions being mounted on the upper and under sides, respectively, of a crosshead of a material testing machine and having a central, axial bore which encloses a barrel provided with an inner linear defining said sample bore; and wherein said temperature sensors are provided at their respective forward ends with a sensing element, and inserted into said upper furnace portion and said furnace zones of said lower furnace portion so that said sensing elements of said sensors in said furnace zones contact the outer circumferential surface of said inner liner of said barrel.

4. The rheometer of claim 1, wherein a hollow cylindrical barrel is disposed inside said furnace and a tubular inner liner is fitted into said barrel to define said sample bore, said inner liner being divided along the length thereof into a plurality of sections.

5. The rheometer of claim 1, wherein said temperature characteristics of said furnace zones are obtained by first energizing said heaters so that the temperature of the inner wall of said sample bore becomes a preset level, whereupon the temperatures of said furnace zones are detected by said temperature sensors and stored in said storing means as temperature characteristics data of said furnace zones related to said preset temperature level of said inner wall of said barrel; repeating the above operation with said heaters so controlled that the temperature of the inner wall of said sample bore becomes progressively different preset levels; and obtaining from said stored temperature characteristics data a characteristic line of the temperature of each of said furnace zones with respect to said preset temperature levels.

6. A device for measuring the temperature in said sample bore of said rheometer as defined in claim 1, comprising a cylindrical stem adapted to be inserted into said sample bore so as to be able to be pulled out therefrom, and a plurality of temperature sensors provided on the outer surface of said stem at those positions thereof which correspond to said furnace zones when said stem is inserted into said sample bore.

7. The device of claim 1, wherein said stem is provided on the outer circumferential surface thereof with a plurality of axially extending, parallel grooves, and said temperature sensors comprising elongated members of different lengths with a temperature sensing element attached to the tip thereof, each of said sensors being fitted in one of said grooves of said stem so that each of said sensing elements are placed at one of those axially spaced-apart positions of said sample bore which correspond to said furnace zones when said stem is inserted into said sample bore of said barrel.

8. A device for measuring the temperature in said sample bore of said rheometer as defined in claim 2, comprising a cylindrical stem adapted to be inserted into said sample bore so as to be able to be pulled out therefrom, and a plurality of temperature sensors provided on the outer surface of said stem at those positions thereof which correspond to said furnace zones when said stem is inserted into said sample bore.

9. A device for measuring the temperature in said sample bore of said rheometer as defined in claim 3, comprising a cylindrical stem adapted to be inserted into said sample bore so as to be able to be pulled out therefrom, and a plurality of temperature sensors provided on the outer surface of said stem at those positions thereof which correspond to said furnace zones when said stem is inserted into said sample bore.

10. A device for measuring the temperature in said sample bore of said rheometer as defined in claim 4, comprising a cylindrical stem adapted to be inserted into said sample bore so as to be able to be pulled out therefrom, and a plurality of temperature sensors provided on the outer surface of said stem at those positions thereof which correspond to said furnace zones when said stem is inserted into said sample bore.

11. A device for measuring the temperature in said sample bore of said rheometer as defined in claim 5, comprising a cylindrical stem adapted to be inserted into said sample bore so as to be able to be pulled out therefrom, and a plurality of temperature sensors provided on the outer surface of said stem at those positions thereof which correspond to said furnace zones when said stem is inserted into said sample bore.

12. The device of claim 2, wherein said stem is provided on the outer circumferential surface thereof with a plurality of axially extending, parallel grooves, and said temperature sensors comprising elongated members of different lengths with a temperature sensing element attached to the tip thereof, each of said sensors being fitted in one of said grooves of said stem so that each of said sensing elements are placed at one of those axially spaced-apart positions of said sample bore which correspond to said furnace zones when said stem is inserted into said sample bore of said barrel.

13. The device of claim 3, wherein said stem is provided on the outer circumferential surface thereof with a plurality of axially extending, parallel grooves, and said temperature sensors comprising elongated members of different lengths with a temperature sensing element attached to the tip thereof, each of said sensors being fitted in one of said grooves of said stem so that each of said sensing elements are placed at one of those axially spaced-apart positions of said sample bore which correspond to said furnace zones when said stem is inserted into said sample bore of said barrel.

14. The device of claim 4, wherein said stem is provided on the outer circumferential surface thereof with a plurality of axially extending, parallel grooves, and said temperature sensors comprising elongated members of different lengths with a temperature sensing element attached to the tip thereof, each of said sensors being fitted in one of said grooves of said stem so that each of said sensing elements are placed at one of those axially spaced-apart positions of said sample bore which correspond to said furnace zones when said stem is inserted into said sample bore of said barrel.

15. The device of claim 5, wherein said stem is provided on the outer circumferential surface thereof with a plurality of axially extending, parallel grooves, and said temperature sensors comprising elongated members of different lengths with a temperature sensing element attached to the tip thereof, each of said sensors being fitted in one of said grooves of said stem so that each of said sensing elements are placed at one of those axially spaced-apart positions of said sample bore which correspond to said furnace zones when said stem is inserted into said sample bore of said barrel.

* * * * *